United States Patent
Nezafat et al.

(10) Patent No.: US 8,457,711 B2
(45) Date of Patent: Jun. 4, 2013

(54) MAGNETIC RESONANCE IMAGING OF CORONARY VENOUS STRUCTURES

(75) Inventors: Reza Nezafat, Newton, MA (US); Warren Manning, Natick, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1183 days.

(21) Appl. No.: 12/011,992

(22) Filed: Jan. 30, 2008

(65) Prior Publication Data

US 2008/0221429 A1 Sep. 11, 2008

Related U.S. Application Data

(60) Provisional application No. 60/898,975, filed on Feb. 1, 2007.

(51) Int. Cl.
*A61B 5/05* (2006.01)

(52) U.S. Cl.
USPC .......................... 600/410; 600/407; 600/413

(58) Field of Classification Search
USPC .. 600/410, 407, 408, 411–423; 324/306–309, 324/318–322
See application file for complete search history.

(56) References Cited

U.S. PATENT DOCUMENTS

| | | | |
|---|---|---|---|
| 5,050,609 A | 9/1991 | Balaban et al. | |
| 5,159,270 A | 10/1992 | Sepponen | |
| 5,250,898 A | 10/1993 | Hu et al. | |
| 5,270,652 A | 12/1993 | Dixon et al. | |
| 5,315,997 A | 5/1994 | Widder et al. | |
| 5,320,099 A * | 6/1994 | Roberts et al. | 600/413 |
| 5,339,035 A | 8/1994 | Schneider et al. | |
| 5,423,317 A | 6/1995 | Iijima et al. | |
| 5,483,163 A | 1/1996 | Wen et al. | |
| 5,488,298 A * | 1/1996 | Wright et al. | 324/309 |
| 5,498,962 A | 3/1996 | Sepponen | |
| 5,557,202 A | 9/1996 | Miyazaki et al. | |
| 5,627,468 A | 5/1997 | Kojima et al. | |
| 5,682,891 A | 11/1997 | Sonoki et al. | |
| 5,792,054 A | 8/1998 | Kouwenhoven et al. | |
| 5,810,728 A | 9/1998 | Kuhn | |
| 5,846,197 A | 12/1998 | Edelman | |

(Continued)

OTHER PUBLICATIONS

Abraham, et al. "Cardiac Resynchronization in Chronic Heart Failure," *N End J Med*; 346(24):1845-1853 (2002).

Aletras, et al., "DENSE: Displacement Encoding with Stimulated Echoes in Cardiac Functional MRI,"*J Magn Reson*; 137:247-252 (1999).

(Continued)

*Primary Examiner* — Unsu Jung
*Assistant Examiner* — Daniel Huntley
(74) *Attorney, Agent, or Firm* — Hamilton, Brook, Smith & Reynolds, P.C.

(57) ABSTRACT

A method and system for magnetic resonance imaging comprises applying at least one radiofrequency magnetization transfer (MT) pulse to a coronary venous region of a subject positioned within a magnetic field, and acquiring magnetic resonance imaging data from the coronary venous region to produce an image of a coronary venous structure. This technique can be utilized as part of a 3D free-breathing, ECG-triggered gradient-echo Cartesian acquisition of the coronary region. One or more magnetization transfer (MT) preparation pulses are used to enhance the contrast between venous blood and myocardium. The MT preparation results in myocardial signal suppression without any significant signal loss in the arterial or venous blood so as to maintain venous blood signal-to-noise ratio while improving contrast between myocardium and veins. The image of a coronary venous structure can be acquired in connection with an interventional cardiovascular procedure, such as a cardiac resynchronization therapy.

33 Claims, 9 Drawing Sheets

U.S. PATENT DOCUMENTS

| | | | |
|---|---|---|---|
| 5,926,021 | A | 7/1999 | Hennig |
| 5,999,839 | A | 12/1999 | Hardy et al. |
| 6,023,634 | A | 2/2000 | Hanawa et al. |
| 6,038,466 | A | 3/2000 | Haselhoff |
| 6,192,264 | B1 | 2/2001 | Foo et al. |
| 6,246,897 | B1 | 6/2001 | Foo et al. |
| 6,265,875 | B1 | 7/2001 | Foo et al. |
| 6,289,232 | B1 | 9/2001 | Jakob et al. |
| 6,320,377 | B1 | 11/2001 | Miyazaki et al. |
| 6,377,835 | B1 | 4/2002 | Schoenberg et al. |
| 6,384,601 | B1 | 5/2002 | Weisler et al. |
| 6,388,442 | B1 | 5/2002 | Uetake et al. |
| 6,408,201 | B1 | 6/2002 | Foo et al. |
| 6,645,144 | B1 | 11/2003 | Wen et al. |
| 6,741,880 | B1 | 5/2004 | Foo et al. |
| 6,781,375 | B2 | 8/2004 | Miyazaki et al. |
| 6,782,286 | B2 | 8/2004 | Miyazaki |
| 6,801,800 | B2 | 10/2004 | Miyazaki et al. |
| 6,850,793 | B1 | 2/2005 | Miyazaki et al. |
| 6,963,769 | B1 | 11/2005 | Balaban et al. |
| 6,980,845 | B1 | 12/2005 | Alsop |
| 6,995,559 | B2 | 2/2006 | Agilandam et al. |
| 7,064,545 | B2 | 6/2006 | Zaharchuk et al. |
| 7,082,326 | B2 | 7/2006 | Johansson |
| 7,116,104 | B2 | 10/2006 | Reddy et al. |
| 2002/0188190 | A1* | 12/2002 | Kassai et al. ............ 600/410 |
| 2005/0059881 | A1 | 3/2005 | Balaban et al. |
| 2006/0020197 | A1* | 1/2006 | Gupta et al. ............ 600/410 |
| 2006/0253015 | A1 | 11/2006 | Nezafat et al. |
| 2007/0038077 | A1* | 2/2007 | Wiethoff et al. ........ 600/420 |
| 2009/0138058 | A1* | 5/2009 | Cooke et al. .............. 607/5 |

OTHER PUBLICATIONS

Alonso, et al, "Six Year Experience of Transvenous Left Ventricular Lead Implantation for Permanent Biventricular Pacing in Patients With Advanced Heart Failure: Technical Aspects," *Heart*; 86(4):405-410 (2001).

Bakker, et al, "Biventricular pacing in end-stage heart failure improves functional capacity and left ventricular function," *J Interv Card Electrophysiol*; 4(2):395-404 (2000).

Balaban, et al., "Magnetization Transfer Contrast in Magnetic Resonance Imaging," *Magn Reson Q*; 8(2):116-137 (1992).

Bax, et al., "Cardiac Resynchronization Therapy: Part I—Issues Before Device Implantation," *J Am Coll Cardio*; 46(12):2153-2167 (2005).

Bax, et al., "Cardiac Resynchronization Therapy: Part 2—Issues During and After Device Implantation and Unresolved Questions," *J. Am Coll Cardio*; 46(12):2168-2182 (2005).

Botnar, et al., "Coronary Magnetic Resonance Angiography," *Cardiol Rev*; 9:77-87 (2001).

Botnar, et al., "Improved Coronary Artery Definition with T2-weighted, free-breathing, three-dimensional Coronary MRA," *Circulation*; 99:3139-3148 (1999).

Brittain, et al., "Coronary Angiography with Magnetizaton-prepped T2 Contrast," *Magn Reson Med*; 33(5):689-696 (1995).

Butter, et al., "Human Experience with Transvenous Biventricular Defibrillation Using an Electrode in a Left Ventricular Vein," *Pacing Clin Electrophysiol*; 25(3):324-331 (2002).

Cappato, et al., "Mapping of the Coronary Sinus and Great Cardiac Vein Using a 2-French Electrode Catheter and a Right Femoral Approach," *J Cardiovasc Electrophysiol*; 8(4):371-376 (1997).

Cazeau, et al., "Four Chamber Pacing in Dilated Cardiomyopathy," *Pacing Clin Electrophysiol*; 17(11 pt 2):1974-1979 (1994).

Daubert, et al., "Cardiac Resynchronisation Therapy in Heart Failure: Current Status," *Heart Fail Rev*; 11(2):147-154 (2006).

Daubert, et al., "Permanent Left Ventricular Pacing with Transvenous Leads Inserted into the Coronary Veins," *Pacing Clin Electrophysiol*; 21(1 Pt 2): 239-245 (1998).

de Paola, et al., "Angiographic and Electrophysiological Substrates for Ventricular Tachycardia Mapping through the Coronary Veins," *Heart*; 79(1):59-63 (1998).

Etienne, et al., "Soap-Bubble" visualization and Quantitative Analysis of 3D Coronary Magnetic Resonance Angiograms, *Magn Reson Med*; 48(4):658-666 (2002).

Fischer, et al., "Novel real-time R-wave Detection Algorithm Based on the Vectorcardiogram for Accurate Gated Magnetic Resonance Acquisitions," *Magn Reson Med*; 42(2):361-370 (1999).

Gerber, et al., "Evaluation of the Coronary Venous System Using Electron Beam Computed Tomography," *Int J Cardiovasc Imaging*; 17(1):65-75 (2001).

Gerber, et al., "The Coronary Venous System: An Alternative Portal to the Myocardium for Diagnostic and Therapeutic Procedures in Invasive Cardiology," *Curr Interv Cardiol Rep*; 2(1):27-37 (2000).

Gutierrez, et al., "Distortion Correction, Calibration, and Registration: Towards an Integraged MR and X-Ray Interventional Suite," *Medical Imaging, Visualization, Image-Guided Procedures, and Display, Proc. of SPIE*; 5744:146-156 (2005).

Haissaguerre, et al., "Radiofrequency Catheter Ablation of Left Lateral Accessory Pathways via the Coronary Sinus," *Circulation*; 86(5):1464-1468 (1992).

Hare, "Cardiac-Resynchronization Therapy for Heart Failure," *J Engl J Med*; 346(24):1902-1905 (2002).

Jais, et al., "Clementy J. Endocardial Biventricular Pacing," *Pacing Clin Electrophysiol*; 21(11 Pt 1):2128-2131 (1998).

Kar, et al., "Coronary Veins: An Alternate Route to Ischemic Myocardium," *Heart Lung*; 21(2):148-157 (1992).

Kim et al., "Relationship of MRI Delayed Contrast Enhancement to Irreversible Injury, Infarcet Age, and Contractile Function," *Circulation*; 100(19):1992-2002 (1999).

Kusano, et al., "Catheter Ablation of an Epicardial Accessory Pathway via the Middle Cardiac Vein Guided by Monophasic Action Potential Recordings," *Europace*; 3(2):164-197 (2001).

Lardo, et al., "Magnetic Resonance Imaging Assessment of Ventricular Dyssynchrony: Current and Emerging Concepts," *J Am Coll Cardiol*; 46(12):2223-2228 (2005).

Li, et al., "Coronary Arteries: Three-Dimensional MR Imaging with Fat Saturation and Magnetization Transfer Contrast," *Radiology*; 187(2):401-406 (1993).

Morin, et al., "Radiation dose in Computed Tomography of the Heart," *Circulation*; 107(6):917-922 (2003).

Muhlenbruch, et al., "Imaging of the Cardiac Venous System: Comparison of MDCT and Conventional Angiography," *AJR Am J Roentgenol*; 185(5):1252-1257 (2005).

Nezafat, et al., "B1-Insensitive T2 Preparation for Improved Coronary Magnetic Resonance Angiography at 3 T.," *Magn Reson Med*; 55:858-864 (2006).

Oesterle, et al., "Percutaneous in Situ Coronary Venous Arterialization: Report of the First Human Catheter-based Coronary Artery Bypass," *Circulation*: 103(21):2539-2543 (2001).

Ryf et al., "Spiral MR Myocardial Tagging," *Magn Reson Med*; 51:237-242 (2004).

Sanders, et al., "Electrical Disconnection of the Coronary Sinus by Radiofrequency Catheter Ablation to Isolate a Trigger of Atrial Fibrillation," *J Cardiovasc Electrophysiol*; 15(3):364-368 (2004).

Schaffler, et al., "Imaging the Coronary Venous Drainage System Using Electron-Beam CT.," *Surg Radiol Anat*; 22(1)35-39 (2000).

Shea, et al., "Three-dimensional True-FISP Imaging of the Coronary Arteries: Improved Contrast with T2-preparation," *J Magn Reson Imaging*; 15:597-602 (2002).

Singh, et al., "The Coronary Venous Anatomy: A Segmental Approach to Aid Cardiac Resynchronization Therapy," *J Am Coll Cardiol*; 46(1):68-74 (2005).

Stellbrink, et al., "Transcoronary Venous Radiofrequency Catheter Ablation of Ventricular Tachycardia," *J Cardiovasc Electrophysiol*; 8(8):916-921 (1997).

Thompson, et al., "Percutaneous Transvenous Cellular Cardiomyoplasty. A Novel Nonsurgical Approach for Myocardial Cell Transplantation," *J Am Coll Cardiol*; 41(11):1964-1971 (2003).

Valls-Bertault, et al., "Adverse Events with Transvenous Left Ventricular Pacing in Patients with Severe Heart Failure: Early Experience from a Single Centre," *Europace*; 3(1):60-63 (2001).

Wolff, "Magnetization Transfer Contrast (MTC) and Tissue Water Proton Relaxation in Vivo," *Magn Reson Med*; 10(1):135-144 (1989).

Wolff, "Magnetization Transfer Imaging: Practical Aspects and Clinical Applications," *Radiology*; 192(3):593-599 (1994).

\* cited by examiner

MAGNETIC RESONANCE IMAGING OF CORONARY VENOUS STRUCTURES

RELATED APPLICATION

This application claims the benefit of U.S. Provisional Application No. 60/898,975 filed on Feb. 1, 2007.

The entire teachings of the above application are incorporated herein by reference

BACKGROUND OF THE INVENTION

Knowledge of coronary vein anatomy is becoming increasingly important for diagnostic and interventional cardiac procedures including epicardial radiofrequency ablation, retrograde perfusion therapy in high-risk or complicated coronary angioplasty, arrhythmia assessment, stem cell delivery, coronary artery bypass surgery and cardiac resynchronization therapy (CRT). Congestive heart failure currently afflicts over 5 million Americans. In patients with severe congestive heart failure, CRT has been proven as an adjuvant therapy to pharmacological treatment. In CRT, simultaneous pacing of the right ventricle and left ventricle, or pacing the left ventricle alone, results in hemodynamic improvements and restoration of a more physiological contract pattern. One of the technical difficulties of CRT is in achieving effective, safe and permanent pacing of the left ventricle. Three methods have been proposed for implantation of a pacemaker lead in the left ventricle: (I) an epicardial route via thoracotomy, (II) left ventricle endocardial pacing via trans-septal catheterization, and (III) transvenous implantation through the coronary sinus using an available posterolateral coronary vein branch. Transvenous coronary sinus pacing is the most common technique as it has the least procedural risk, but it is associated with long procedure times, extensive radiation exposure from fluoroscopy, implantation failure and lead dislodgement from the left ventricle. Two of the major difficulties of the transvenous approach are the small number of coronary vein branches adjacent to an appropriate left ventricle wall and variation in coronary vein anatomy among patients. Ideally, coronary venous morphology should be assessed non-invasively prior to a CRT procedure to determine whether epicardial or transvenous lead placement would be more appropriate for a particular patient.

Currently, two modalities are used for imaging of coronary venous anatomy: X-ray fluoroscopy and multi-detector computed tomography (MDCT). Invasive coronary X-ray venography is routinely performed immediately prior to placement of a left ventricle pacemaker lead. A balloon-tipped catheter is inserted into the coronary sinus, followed by injection of a contrast agent after balloon occlusion of the coronary sinus close to its ostium. MDCT can also be used to obtain detailed noninvasive imaging of the coronary veins. The major disadvantage of MDCT is the radiation dose received in addition to the already significant dose that the patient later receives during the interventional procedure. In addition, MDCT coronary venography requires administration of a nephrotoxic iodinated contrast to a population in which renal dysfunction is common.

SUMMARY OF THE INVENTION

Magnetic resonance (MR) imaging, with its flexible image contrast and customizable acquisition schemes, has the potential to be the non-invasive modality of choice because in addition to imaging coronary vein anatomy, MR can also provide information about left ventricle scarring and dyssynchrony. Developments in the field of coronary artery magnetic resonance imaging can provide a foundation upon which to tailor new techniques for imaging the adjacent coronary veins. Although there are significant similarities between coronary artery and vein imaging using magnetic resonance, there are also considerable differences. In coronary artery imaging, the primary goal is the detection of stenoses. However, a coronary vein imaging technique is preferably designed for the assessment of location, angulation, tortuosity and diameters of feeding branches of the coronary sinus. Thus, a lower spatial resolution may be sufficient. However, coronary venous blood has a short $T_2$ relaxation time compared to arterial blood, which makes the use of established contrast preparation sequences based on $T_2$ impractical. The conventional techniques for magnetic resonance imaging coronary arteries are optimized to highlight the signal of oxygenated arterial blood relative to the surrounding tissue, and tend to suppress the signal from coronary venous structures, rendering them indistinguishable from the surrounding myocardium. Thus, conventional coronary MRI methods are not useful for imaging coronary venous structure, and have not generally been employed, for instance, in connection with an interventional cardiovascular procedure.

According to one aspect of the invention, a method and system for magnetic resonance imaging comprises applying at least one radiofrequency magnetization transfer (MT) pulse to a coronary venous region of a subject positioned within a magnetic field; and acquiring magnetic resonance imaging data from the coronary venous region to produce an image of a coronary venous structure.

In one aspect, the present invention relates to a high-resolution coronary magnetic resonance vein imaging sequence that can be advantageously utilized as part of a 3D free-breathing, ECG-triggered gradient-echo Cartesian acquisition of the coronary region. In coronary artery imaging, typically a $T_2$ preparation sequence is used to improve blood-myocardium contrast. However, this preparation sequence suppresses coronary vein signals due to the short $T_2$ of deoxygenated coronary venous blood ($T_2$=35 milliseconds).

The present invention utilizes at least one magnetization transfer (MT) prepulse to enhance the contrast between venous blood and myocardium. The MT preparation results in myocardial signal suppression without any significant signal loss in the arterial or venous blood so as to maintain venous blood signal-to-noise ratio while improving contrast between myocardium and veins. The signal enhancement is based on the exchange of magnetization between water and macromolecular protons in the myocardium. By designing the proper parameters of the MT preparation pulse(s), the macromolecular pool is saturated by a process called magnetization exchange. There is no significant decrease in venous blood signal level while there is a significant decrease in the myocardial signal, resulting in a desirable contrast-to-noise between a coronary venous structure and myocardium. In a preferred embodiment, the coronary venous structure comprises one or more of a coronary sinus, a lateral vein and a posterior vein. The image of a coronary venous structure can be acquired in connection with an interventional cardiovascular procedure, such as a cardiac resynchronization therapy.

In a preferred embodiment, the MT preparation pulse is off-set from the resonant frequency of water within the magnetic field. Preferably, the MT pulse is offset from the resonant frequency of water by 500 Hz or less, and preferably by between 300 and 500 Hz. An MT preparation sequence can comprise a train of radiofrequency MT pulses that is applied to the subject prior to MR data acquisition. In one embodiment, the train of pulses comprises 8-10 pulses, and each pulse in the train can have a pulse duration between about 10 and 20 milliseconds. Each pulse in the train of MT pulses can have a flip angle between about 800 degrees and 1000 degrees. The shape of the MT pulses according to the present invention can comprise, for example, Gaussian, Fermi, Sinc, and Gaussian-weighted Sinc.

In one embodiment, all pulses in an MT preparation pulse train have a substantially identical shape and frequency response. In other embodiments, the MT pulses can vary in at least one of their shape and their frequency response across the train of pulses.

The MT preparation pulse or pulse sequence is preferably coordinated to the cardiac cycle of the subject, and can be initiated in response to a trigger signal from an electrocardiogram device. Following the application of one or more MT preparation pulses, magnetic resonance imaging data can be acquired with a gradient-echo acquisition sequence. In certain embodiments, a respiratory navigation can be performed between the application of one or more MT pulses and the acquisition of the magnetic resonance imaging data. In addition, a radiofrequency pulse to promote fat saturation in the coronary venous region can also be applied between the MT pulse(s) and the acquisition of the magnetic resonance imaging data. Preferably, during the imaging sequence, including the application of one or more MT preparation pulses, the specific absorption rate of the subject is less than about 1 watt per kilogram, and even more preferably less than about 0.8 watts per kilogram.

According to another aspect of the invention, a magnetic resonance imaging system comprises a system controller configured to define a magnetization transfer (MT) pulse; a radiofrequency coil that is controlled by the system controller to produce radiofrequency pulses that are transmitted to a coronary venous region of a subject located in a magnetic field, the system controller controlling the radiofrequency coil to produce at least one MT pulse followed by one or more imaging pulses; and a receiver that acquires magnetic resonance imaging data in response to the imaging pulses to produce an image of a coronary venous structure.

According to yet another aspect, a computer readable medium has a computer executable program for performing a magnetic resonance imaging (MRI) sequence that comprises applying at least one radiofrequency magnetization transfer (MT) pulse to a coronary venous region of a subject located in a magnetic field subject and subsequent to the application of the at least one MT pulse, acquiring magnetic resonance imaging data to produce an image of a coronary venous structure.

According to another aspect of the invention, the MT preparation pulse may be on-resonance. Various other methods available in the art may also be employed for the preparation of MT contrast.

According to another embodiment of the invention, images may be acquired for localization and navigator positioning using a steady-state free precession (SSFP) sequence. In another embodiment, images may be acquired using a 3D gradient-echo (GRE) sequence. Other imaging sequences available in the art may also be used for image acquisition.

According to another embodiment, images may be acquired using a thin 3D slab placed on the lateral and posterior wall of the left ventricle. Multi-slab image acquisition techniques may also be used. In another embodiment, whole heart acquisition techniques may be employed.

According to yet another embodiment of the invention, a respiratory navigator-echo for motion compensation may be used. In other embodiments, available methods in the art, such as breath-hold techniques may be employed.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1:
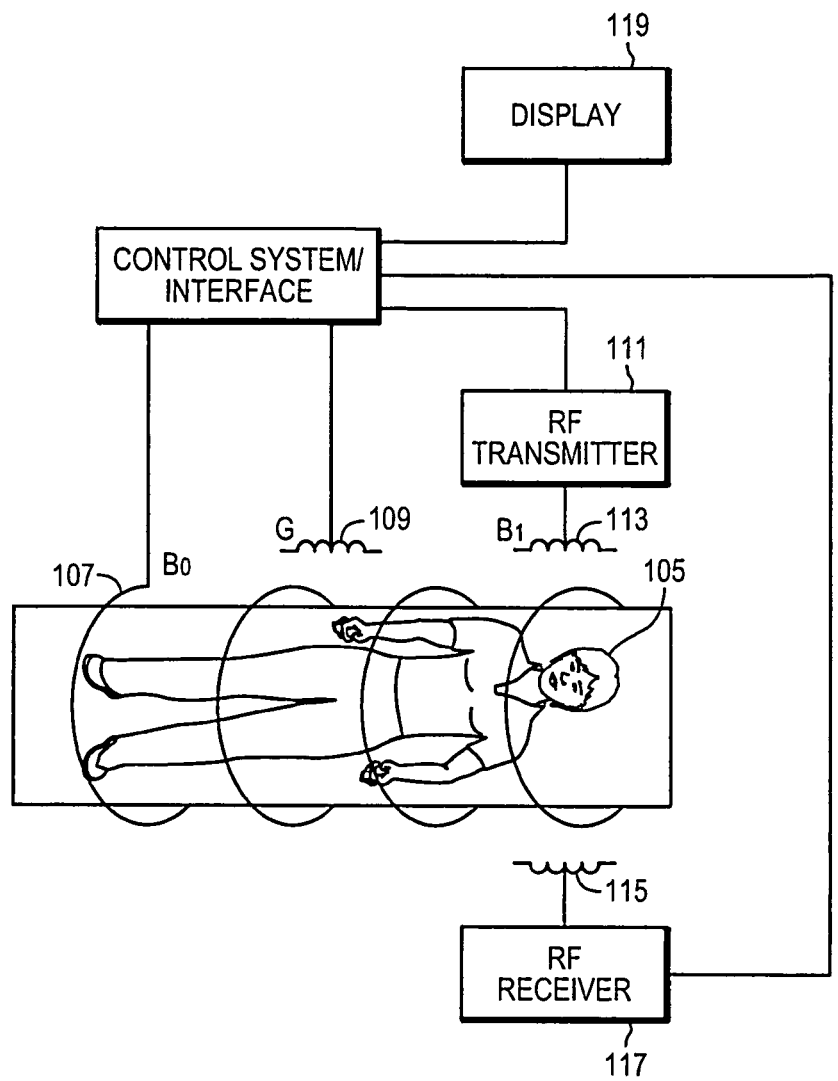
FIG. 1 is a schematic illustration of a magnetic resonance (MR) imaging system.

A representative magnetic resonance imaging (MRI) system 101 is shown in FIG. 1. The system includes a control system/interface 103 that is programmed with a series of commands to perform a sequence of imaging steps. The controller 103 controls a field coil 107 for producing a stationary magnetic field $B_0$, one or more gradient coils 109 for producing gradient magnetic fields, G, and a radiofrequency (RF) transmitter 111 configured to generate RF pulses that are applied to a transmitter coil 113 to produce an RF magnetic field, $B_1$. A receiver coil 115 detects changes in the magnetization of the object being imaged, and transmits these signals to an RF receiver 117. The receiver 117 converts these signals into electrical signals that can be processed by the control system 103 to produce an image of an object 105 located within the MRI system. The image can be viewed on a display apparatus 119.

The principles of MR imaging are well known. An object 105 to be imaged, such as a human or animal body or body part, is placed in a generally stationary and homogenous magnetic field, $B_0$, resulting in a net magnetization in the object 105 in the direction of the magnetic field. This magnetization is manipulated by applying RF pulses from the RF transmitter coil 113, and detecting the changes in object magnetization at the receiver 117. The field gradient, G, exposes the object 105 to non-uniform magnetic field and enables the selection of a particular slice of the object 105 for imaging. A well-chosen sequence of RF pulses and field gradient pulses cause the object to emit magnetic resonance signals that provide information about the chemical and physical structure of the object that can be represented as an image of the internal structure of the object 105.

The control sequence for a particular imaging application is typically stored by the control system 103 for retrieval from a computer readable media, and can be selected by a clinician by a user interface.

It will be understood that the present coronary MR imaging sequences can be implemented on various MR imaging systems suitable for medical imaging applications by readily-implemented modifications to the command sequences if the devices. One preferred system for practicing the present invention is the 1.5T INTERA ACHIEVA system from Philips Medical Systems, Best, NL, with a five-element cardiac phased-array receiver coil, and vector electrocardiographic (VCG) R-wave triggering.

Figure 2:
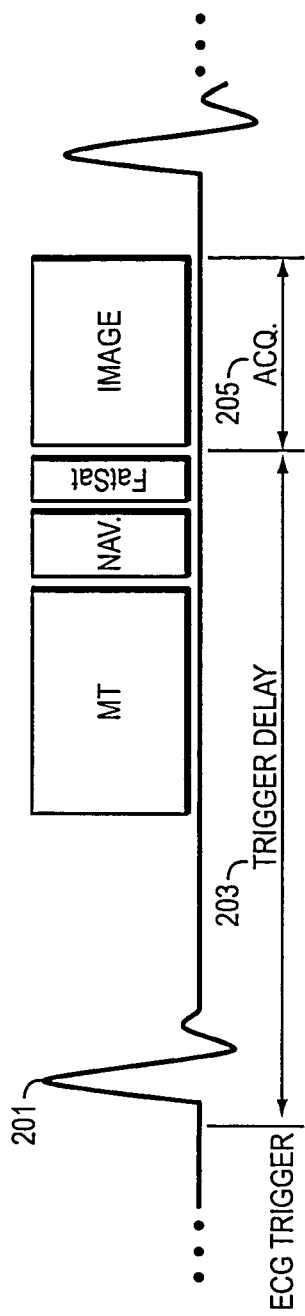
FIG. 2 illustrates a coronary vein imaging sequence according to one aspect of the present invention.

In one embodiment of the invention, a high resolution coronary MR vein imaging sequence is based on a 3D gradient-echo free-breathing navigator-echo gated with fat saturation, vector ECG-triggered Cartesian acquisition. FIG. 2 shows the schematic of the developed sequence. Although a $T_2$ preparation sequence is commonly used to improve blood-myocardium contrast in coronary artery imaging, the prep pulse suppresses coronary vein signals due to the short $T_2$ (~35 milliseconds) of deoxygenated venous blood. In contrast, the present invention utilizes a magnetization transfer (MT) preparation pulse for contrast enhancement. This preparation advantageously provides suppression of the myocardial signal with minimum saturation of the venous blood so as to maintain venous blood signal-to-noise ratio. This technique provides improved delineation of the coronary venous morphology, with a particular emphasis on the posterior and lateral wall of the myocardium, since the pacing lead in cardiac resynchronization therapy is typically placed in the posterior-lateral venous branch.

A representative pulse sequence for coronary MR vein imaging is shown in FIG. 2. A trigger pulse 201 is obtained from, for example, an electrocardiogram (ECG). A "trigger delay" period 203 elapses between the trigger pulse 201 and the image data acquisition 205. During this trigger delay period, a series of radiofrequency (RF) preparation pulses are applied to the imaging area. An MT preparation sequence (MT) comprised of a series of off-resonance radiofrequency pulses (e.g., 8-10 pulses) is first applied, followed by a respiratory navigator beam (NAV) for motion compensation and a spectrally-selective RF pulse for saturation of fat signal (FatSat). The train of pulses may comprise 8-10 pulses, and each pulse in the train can have a pulse duration between about 10 and 20 milliseconds. Each pulse in the train of MT pulses can have a flip angle between about 800 degrees and 1000 degrees. During the image acquisition stage 205, a gradient echo acquisition comprised of 10-15 imaging TRs is applied for image acquisition (IMAGE). Fat saturation in coronary vein imaging, especially along the coronary sinus, is generally needed due to the high burden of epicardial fat in the anterior ventricular groove.

The MT preparation sequence achieves contrast enhancement based on the exchange of magnetization between water and macromolecular protons in the myocardium. With MT, a primary objective is to saturate the macromolecular pool by a process called magnetization exchange. The use of magnetization transfer in MR imaging has been discussed, for example, in U.S. Pat. No. 5,050,609 to Balaban et al., the entire teachings of which are incorporated herein by reference. Two important elements to consider in the design of off-resonance RF pulses for MT are: (i) negligible flip angle at the Larmor frequency of water and (ii) low specific absorption rate (SAR). With these concepts in mind, a train of spectrally-selective off-resonance RF pulses were developed to create an MT exchange phenomena for improved venous blood-myocardium contrast.

Figure 3B:
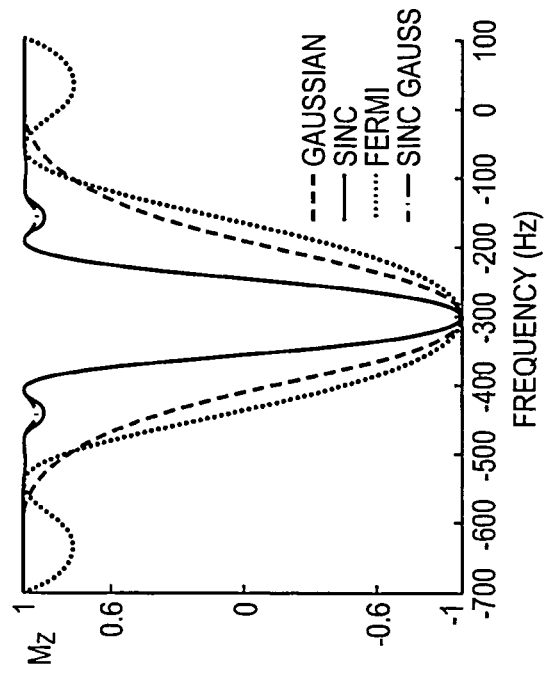
FIG. 3B illustrates the frequency responses of the pulses of FIG. 3A.
Figure 3A:
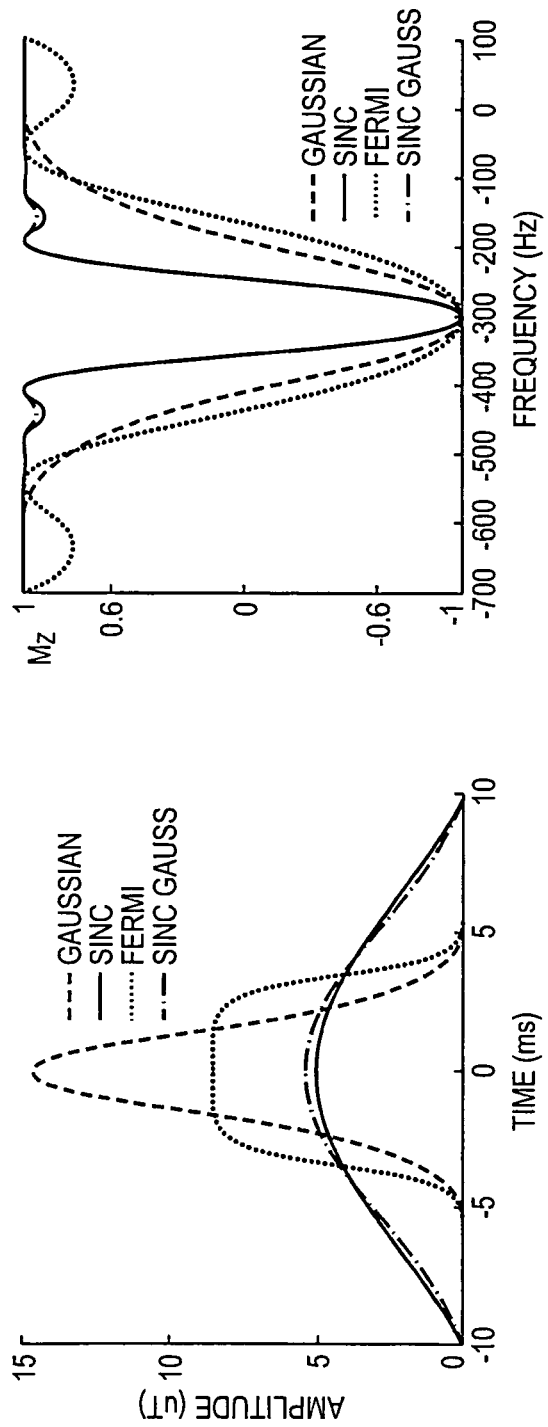
FIG. 3A illustrates the envelope of four magnetization transfer (MT) preparation pulses.

Myocardial signal suppression by the MT preparation is improved if the RF pulses in the preparation sequence have center frequencies close to the Larmor frequency (e.g. 300-500 Hz). However, using such pulses may have adverse effects. The presence of ripples in the stop band of the spectrum of the RF pulse will result in direct irradiation of water pool, i.e. a non-negligible flip angle at the resonant frequency of water, and consequently inhomogenous signal loss, banding artifacts across the image, and saturation of the blood signal. Since the coronary MR vein acquisition is VCG-triggered, there is a long time period prior to the start of image acquisition (>400-500 ms) that is available for preparation sequences. This significant available time allows for flexibility in the design of RF pulses, permitting the use of excitations with better frequency responses (long duration and decreased ripple) and lower SAR (decreased amplitude). Four widely used RF pulse-shapes were investigated for MT contrast: Gaussian, Fermi, Sinc, and Gaussian-weighted-Sinc as shown in FIGS. 3A and 3B. The $B_1$ field of a Gaussian pulse shape of duration T is given by:

$$B_1(t) = \frac{1}{\sqrt{2\pi}\sigma} e^{\frac{t^2}{2\sigma^2}} \quad -\frac{T}{2} < t < \frac{T}{2}$$

where $\sigma$ is the standard deviation and t is time. The pulse duration T is defined by the points in which the $B_1$ field reaches to 0.1% of its maximum (60 dB attenuation). The Fermi pulse shape is given by:

$$B_1(t) = \frac{1}{1+e^{\frac{|t|-t_0}{c}}} \quad -\frac{T}{2} < t < \frac{T}{2}$$

where c and $t_0$ are two pulse parameters which determine the transition width and the pulse width, respectively. The pulse duration was set to have 60 dB attenuation with a pulse width equal to ten times the transition time. The Sinc pulse did not have any side lobes to decrease SAR as shown in FIG. 3B. Numerical simulations were performed comparing these pulses as part of a train of off-resonance RF pulses. The relative SAR and frequency spectrum of each pulse were calculated numerically for a single RF pulse and for a train of 10 consecutive pulses. To calculate the frequency response of each RF pulse simulation of the Bloch equations was performed. Relative SAR of each MT train was determined by numerical calculation. All pulses had equal duration T=20 ms, and flip angle $\alpha$=900°.

In vivo, the optimal parameters for the MT pulses were determined empirically by performing a series of 2D axial mid-ventricular images in two healthy adult subjects. Based on numerical simulation, a Gaussian-weighted-Sinc pulse shape was used in these acquisitions. The venous blood-myocardium signal difference and loss of SNR in the blood signal were used as metrics for the MT preparatory sequence. The number, flip angle and frequency-offset of the MTC were determined in this manner and used in future studies.

Coronary MR Vein Imaging Protocol:

Three-orthogonal stacks of multiple 2D bright blood images were acquired for localization and navigator positioning using a steady-state free precession (SSFP) sequence. Subsequently, VCG triggered, segmented SSFP cine images (TR=2.1 ms, TE=1.3 ms, $\alpha$=60°, temporal resolution of 35.5 ms, spatial resolution of 2×2 mm$^2$ reconstructed to 1.25×1.25 mm$^2$) were acquired at the level of the coronary sinus to calculate the duration of the diastolic rest period best suited for motion-free imaging. The most quiescent period was determined visually with focus placed on minimizing the motion of the coronary sinus. A 3D axial, low resolution, navigator gated, free breathing, MT prepared scan was acquired for localization of the coronary veins. The navigator beam was positioned at the dome of the right hemidiaphragm with an acceptance window of 5 mm, continuous respiratory drift, and RF excitation angle of 25°. Subsequently, the volume for coronary vein MR imaging was prescribed using a 3 point planning tool. The volume covered the coronary sinus and great cardiac vein in order to capture the origin of all tributaries of coronary sinus. 20-30 slices with thickness of 1.5 mm (after zero-filling) were acquired per 3D dataset. For imaging, 10-15 RF excitations (based on subject specific quiescent period) with spoiled gradient-echo readouts ($\alpha$=30°, TR=5.5 ms, TE=1.6 ms) were performed during each R-R interval. A field of view (FOV) of 270 mm×270 mm was imaged with a scan matrix of 272×218. The images were reconstructed to a matrix size of 512×512 with a resultant voxel size of 0.53×0.53×1.5 mm$^3$. Subsequently a coronal scan perpendicular to the coronary sinus with the same imaging parameters as the previous scan was prescribed to image the entire length of tributaries of coronary sinus in lateral and posterior wall of the heart.

Phantom Study

A phantom study was performed to evaluate the efficacy of the MT preparation sequence for coronary MR vein imaging using aqueous gel phantoms containing different concentration of agar. Signal suppression in an agar phantom in the presence of off-resonance irradiation has been associated with an MT effect. Two phantoms were constructed containing 4% and 8% concentration of agar by weight. An additional commercial Gd-DTPA doped water phantom was used as a control. All three phantoms were imaged with and without the MT preparation sequence. The mean and the standard deviation of the signal in each phantom were measured by drawing a region of interest. A 3D gradient echo acquisition similar to one used for in-vivo acquisition with simulated VCG gating signal was used to image the phantoms. Imaging parameters were as follow: $\alpha$=30°, TR=5.8 ms, TE=1.73 ms, 20 slices, spatial resolution of 1.0×1.4 mm$^2$, FOV=390×390 mm$^2$.

In Vivo Study

Coronary MR vein images were acquired in 8 healthy adult subjects (all females, average age 21.2 years old) to study the effect of MT on SNR and blood-myocardium contrast. Images were acquired with and without an MT preparation sequence. Furthermore, images were acquired in additional 10 healthy subjects to investigate scan plane prescription to better assess coronary vein anatomy in the posterior wall. Coronary MR vein imaging was acquired in six CHF patients referred for CRT (5 males, average age 62.5 years old). In the initial 4 patient studies, only images orientated along the coronary sinus was acquired to assess existence and angle of the branching angle of tributaries of the coronary sinus. For 4 out of 6 patients, invasive X-ray balloon venography was also acquired in the electrophysiology lab during CRT transvenous lead placement. X-ray coronary venography was visually compared with MR images. Image analysis including statistical measurements was performed on a stand-alone PC, and images were also multi-planar reconstructed using a research software application, SOAPBUBBLE, described in A. Etienne et al., "'Soap-Bubble' Visualization and Quantitative Analysis of 3D Coronary Magnetic Resonance Angiograms," Magn. Reson. Med. 48(4): 658-666 (2002), the entire teachings of which are incorporated herein by reference.

Statistical Analysis

SNR of venous blood, arterial blood and myocardium was measured by drawing a region of interest in the coronary sinus, left ventricle and myocardium for only healthy subjects. The noise was measured in the airspace across the chest wall. Contrast to noise ratio (CNR) between the venous blood and myocardium was also measured. A two-tailed, paired sample t test was used for comparing the measurements. A P value of <0.05 was considered statistically significant.

Results:

Numerical Study

FIG. 3A shows the envelope of the four preparation MT pulses that were studied for coronary MR vein imaging. FIG. 3B displays the flip angle vs. off-set frequency for each pulse shape. This frequency response shows that the Gaussian-weighted-Sinc and Gaussian pulses have the advantage of negligible ripples outside the saturation band. The relative SAR of Fermi, Gaussian, Sinc, and Gaussian-weighted-Sinc pulses were 100%, 138%, 85%, and 90% respectively. These values show that the Gaussian-weighted-Sinc and Sinc pulses are the most energy efficient pulses among the four pulses studied. Although the Gaussian pulse has a better frequency response compared to the Gaussian-weighted-Sinc pulse, it has significantly higher SAR (52%). Therefore, the individual Gaussian-weighted-Sinc and Sinc pulse display acceptable frequency response and low SAR. Though not shown here, simulation results of the MT preparation sequence consisting of a train of 10 RF pulses shows similar frequency responses to those displayed in FIG. 3B, though with larger ripples. A train of Gaussian-weighted-Sinc pulses with equal parameters (frequency, duration and flip angle) were selected for use in an in vivo imaging study.

Phantom Study

Figure 4:
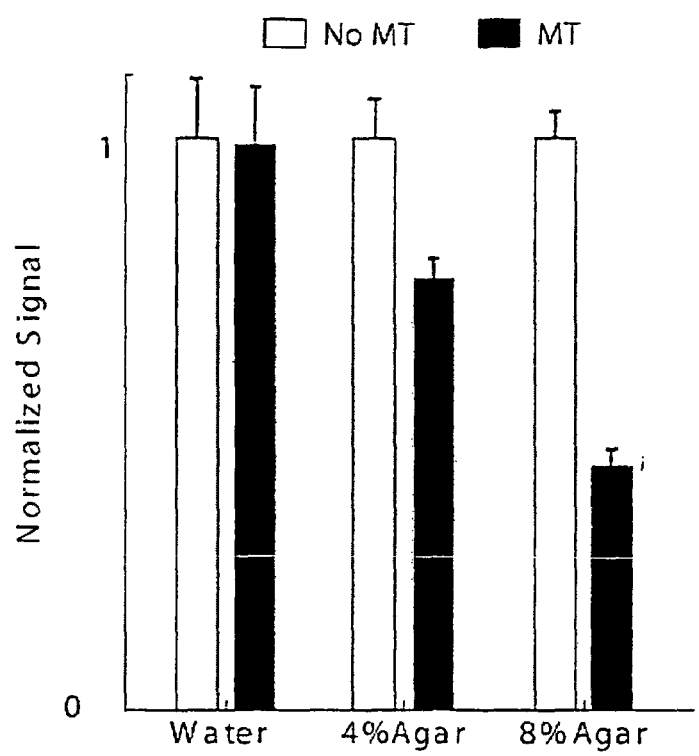
FIG. 4 shows the mean and the standard deviation of a MR signal in agar and water phantoms with and without the MT preparation sequence of the invention.

FIG. 4 shows the mean and the standard deviation of MR signal in a region of interest in agar and water phantom with and without application of the complete MT preparation sequence. There was increased signal suppression in the 8% agar tube relative to the 4% agar tube, as expected with higher MT effects. While the agar phantom shows signal suppression, the water signal did not show any decreases in signal intensity, demonstrating that the selected RF pulse shape and train duration have negligible effects on on-resonance spins. These experiments thereby confirm the ability of the present MT preparation sequence to deliver MT-based contrast enhancement without damaging image quality by disturbing on-resonance spins.

Figure 5:
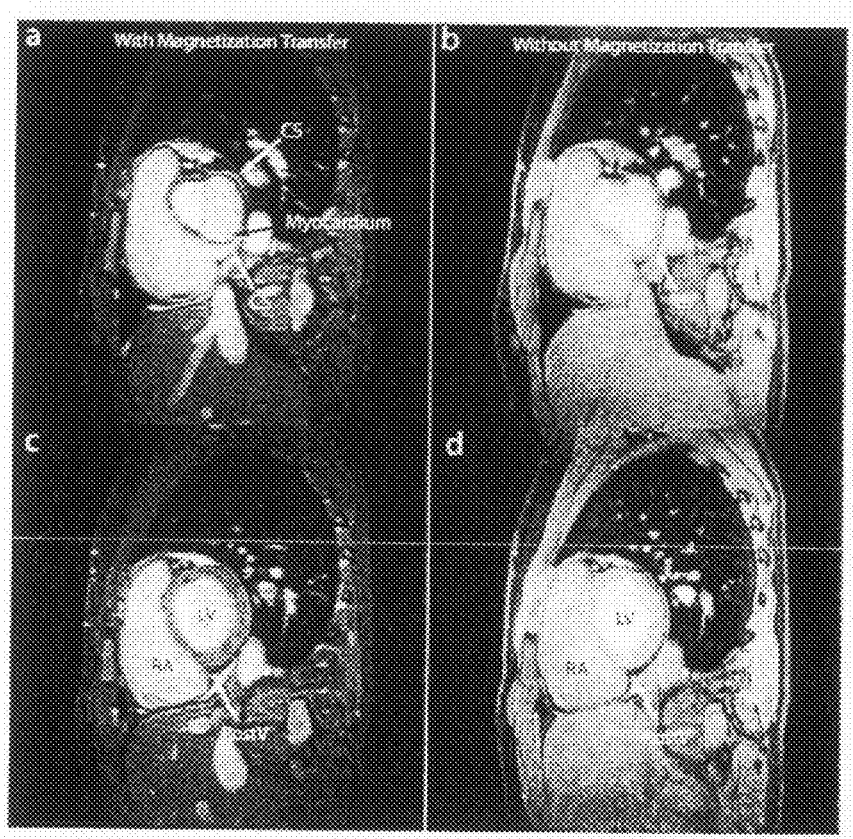
FIGS. 5A-5D are coronary MR vein images with MT contrast enhancement (FIGS. 5A & 5C) and without MT contrast enhancement (FIGS. 5B & 5D) from a healthy adult human subject.
Figure 6:
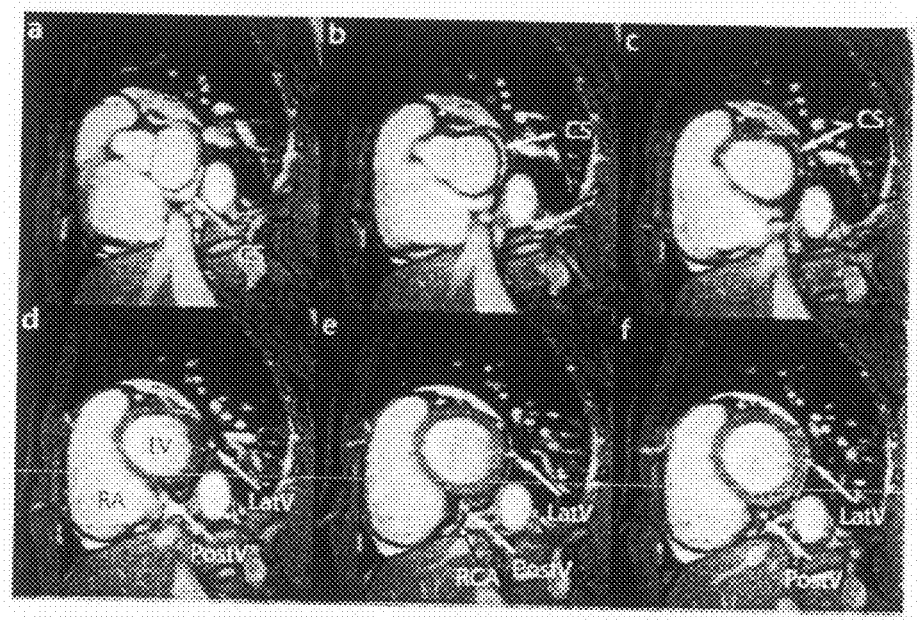
FIGS. 6A-6F are selected coronary MR vein images with MT contrast enhancement taken from a 3D data set from a healthy adult human subject.
Figure 7:
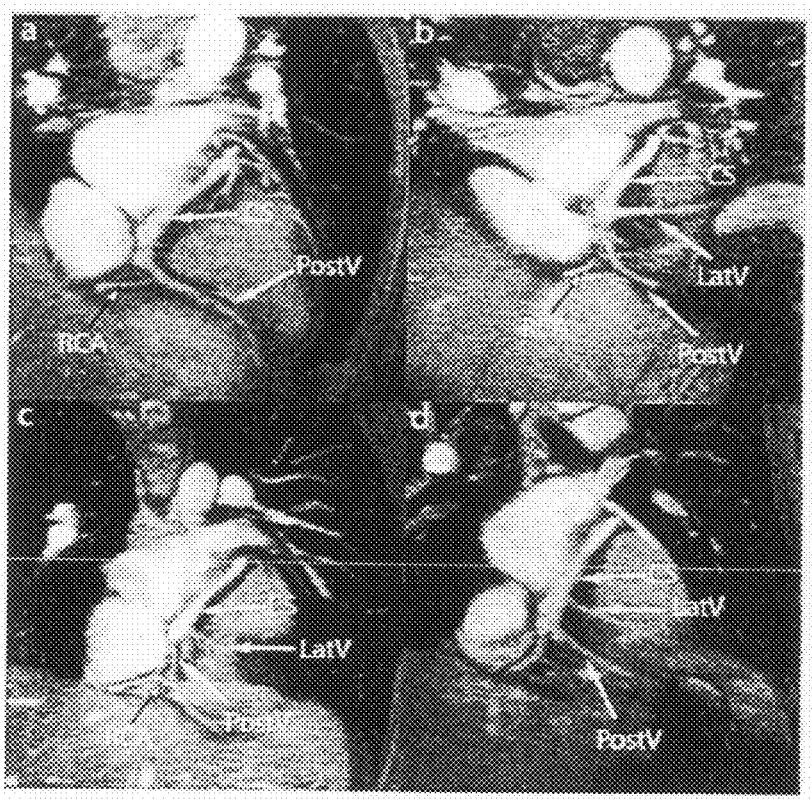
FIGS. 7A-7D show coronary MR vein images with MT contrast enhancement from four different healthy adult human subjects illustrating variations in coronary vein anatomy.
Figure 8:
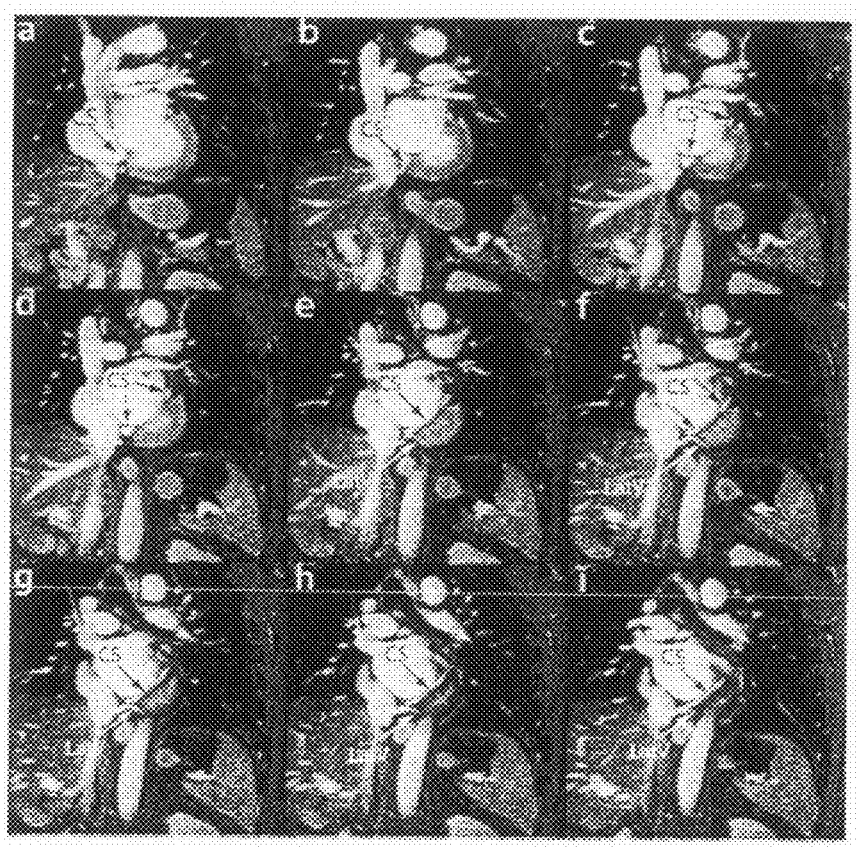
FIGS. 8A-8I show coronary MR vein images of a first congestive heart failure patient referred for cardiac resynchronization therapy.
Figure 9:
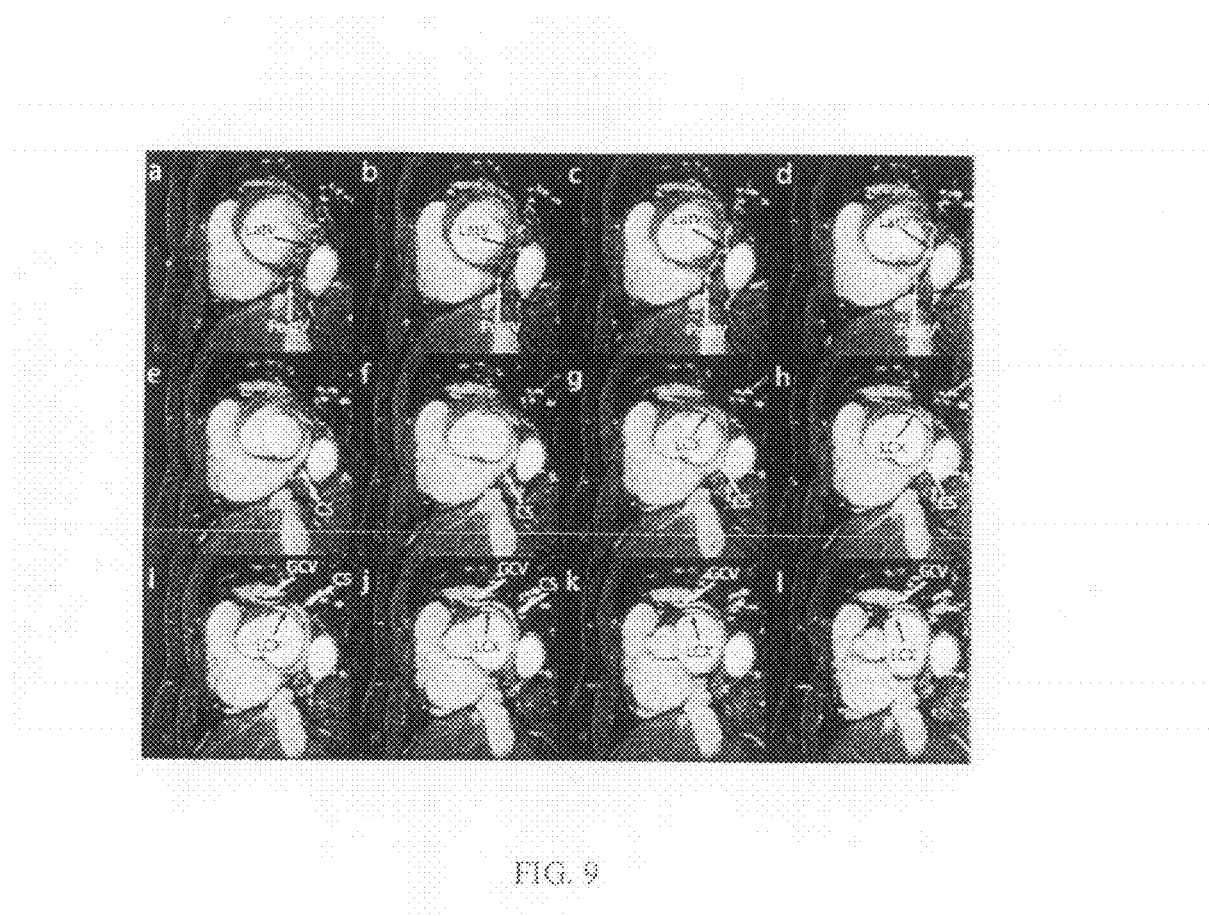
FIGS. 9A-9L show coronary MR vein images of a second congestive heart failure patient referred for cardiac resynchronization therapy.

In Vivo Studies:

FIGS. 5A through 5C compare coronary vein images acquired in healthy adult subjects, demonstrating the efficacy of MT contrast enhancement. The coronary vein images in FIGS. 5A and 5C were acquired using MT for contrast enhancement with the corresponding slice from a non-MT acquisition in FIGS. 5B and 5D. The two slices were selected from a 20 slice coronary vein image acquisition. There is a visible improvement in the contrast between myocardium and blood which enhances the visualization of the venous system. Segments of coronary sinus (CS) and posterior vein (PostV) can be seen as shown by the arrows. The right atrium is labeled RA, and the left ventricle is labeled LV. The myocardial wall is also visible between the coronary sinus (CS) and the left ventricle (LV) blood pool in FIG. 5A.

FIGS. 6A through 6F show coronary MR vein images in a healthy adult subject. Images in A-F are selective slices from a 3D data set of 20 slices acquired along the coronary sinus (CS) which can be easily followed through slices A-C, with posterior vein (PostV) and lateral vein branch (LatV) in D-F. The distal portion of the right coronary artery (RCA) is also visible in FIG. 6E (black arrow).

FIGS. 7A through 7D show the reformatted coronary MR vein images in four different healthy adult subjects acquired using a thin 3D slab placed on the lateral and posterior wall of the left ventricle. These reformatted vein images show variations of the coronary vein anatomy in individuals. For example, in FIG. 7A, the lateral branch of the coronary vein which is commonly used for positioning of the pacing lead does not exist. The posterior and lateral vein together are seen in only <50% of human hearts. Images seen in FIGS. 7A through 7D have varying size, angle and origination of the posterior and lateral branches of the coronary vein system. These variations in coronary venous anatomy show the necessity for non-invasive assessment of anatomical variations in patients undergoing transvenous CRT lead placement.

FIGS. 8A through 8I show coronal views of coronary MR vein for a congestive heart failure patient referred for cardiac resynchronization therapy (CRT). The coronary sinus (CS) and a small lateral vein (LatV) branch with acute take-off angle are clearly identifiable in images 8D-8I. Images were also acquired in a posterior view to image the posterior branch (not shown here). FIGS. 9A-9L show the coronary MR vein of another CHF patient along the CS. The presence of a lateral and posterior branch with relatively large size and favorable angle can be visualized (arrows).

Statistical comparisons of MT contrast enhancement are shown in Table 1. When comparing the image data obtained with MT contrast to non-MT acquisition, there was a significant change in myocardial signal and CNR of venous blood-myocardium with no change in arterial or venous blood SNR. Consistent with prior studies, the myocardium shows significant MT effect, while flowing blood has no MT effect.

The feasibility of coronary MR vein imaging using a MT preparation sequence is demonstrated by numerical simulation, a phantom study and small cohort of healthy adult subjects and CHF patients. The present coronary MR vein imaging technique can be combined with other coronary MR-based measures of cardiac function to complete pre-procedural assessment of CHF patients undergoing CRT. For example, the addition of viability imaging and mechanical dyssynchrony measurements can easily provide an all-around assessment of cardiac status.

There are significant variations in coronary vein anatomy in terms of existence, angulations and size of the tributaries of coronary sinus. In initial testing, patients have been found with unfavorable branches for CRT. In one CHF patient, the transvenous lead placement was unsuccessful due to acute angle of the lateral vein branch. Therefore, the patient was referred for epicardial surgical lead placement after the failed attempt of transvenous placement. This transvenous attempt could have been avoided if an established non-invasive imaging of coronary vein anatomy was performed prior to attempted transvenous implantation. In a second patient, the lateral vein lead was dislodged due to angulations of the lateral branch, which runs almost parallel to the coronary sinus. It is expected that further patient studies imaged with both CMR and X-ray venography will be able to define favorable anatomical criteria for transvenous CRT lead positioning.

A possible concern and limitation of magnetization transfer preparation has been the increase in SAR. With the present coronary vein imaging sequence, the long period of time after VCG trigger permits the application of the multiple high flip angle MT pulses. Furthermore, the RF pulses are designed having long duration to keep the maximum amplitude of each pulse low, further reducing SAR deposition. Finally, the contrast preparation is generally performed only once per cardiac cycle to further reduce SAR. An acquisition performed with 10 optimized RF pulses 20 ms in duration, on a person with a heart rate of 60 BPM and weighting 70 Kg, has an SAR of <0.8 W/Kg. The SAR of the same acquisition without the MT pre-pulses is <0.2 W/Kg. Although there is an expected increase in SAR with the MT preparatory pulses, it is still well below the FDA limit of 4 W/Kg, and well within clinically acceptable SAR limits.

Table 1 shows the signal to noise (SNR) of myocardial, venous and arterial blood and contrast-to-noise (CNR) between venous blood and myocardium in 8 healthy adult subjects. All images were acquired using an MT prepulse comprising 8-10 Gaussian-weighted Sinc RF pulses with offset frequencies of 300-500 Hz, duration of 15-20 milliseconds each and flip angle of 800-1000 degrees. There is no significant change in venous or arterial blood signal level while there is a significant decrease (P<0.001) in the myocardial signal which creates a desirable CNR contrast between venous blood and myocardium.

According to one embodiment, a coronary MR vein imaging methodology is disclosed. Magnetization transfer contrast is used to enhance the contrast between myocardium and venous blood. While MT will reduce the myocardial signal, it has minimal effect on blood signal. This improves the contrast without and venous blood SNR loss. Imaging of coronary vein anatomy would be beneficial in various interventional cardiovascular procedures including CRT. The ability of CMR to combine coronary vein anatomy, function and scar imaging is unique among many imaging modalities. This pre-procedural CMR assessment in CRT patients could have the potential to reduce the high failure rate in this therapy and thereby improve the healthcare of the large CHF population.

TABLE 1

| | with MT contrast | without MT contrast | $P_{value}$ |
|---|---|---|---|
| $SNR_{Myocardium}$ | 26.6 ± 2.24 | 40.12 ± 14.7 | <0.001 |
| $SNR_{Venous\ Blood}$ | 48.81 ± 5.63 | 46.87 ± 15.84 | NS |
| $SNR_{Arterial\ Blood}$ | 53.45 ± 4.54 | 52.25 ± 16.32 | NS |
| $CNR_{Venous\ Blood-Myocardium}$ | 21.74 ± 4.62 | 6.5 ± 4.7 | <0.001 |

According to another embodiment, the MT preparation pulse may be on-resonance. Various other methods available in the art may also be employed for the preparation of MT contrast.

According to yet another embodiment, images may be acquired for localization and navigator positioning using a steady-state free precession (SSFP) sequence. Other imaging sequences available in the art may also be used for image acquisition.

According to another embodiment, images may be acquired using a thin 3D slab placed on the lateral and posterior wall of the left ventricle. Multi-slab image acquisition techniques may also be used. In another embodiment, whole heart acquisition techniques may be employed.

According to yet another embodiment of the invention, a respiratory navigator-echo for motion compensation may be used. In other embodiments, available methods in the art, such as breath-hold techniques may be employed.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for magnetic resonance imaging comprising:
applying a train of radiofrequency magnetization transfer (MT) pulses having a frequency that is offset from resonant frequency of water within a magnetic field to a coronary venous region of a subject positioned within the magnetic field, the MT pulses applied to suppress a magnetic resonance signal from myocardial tissue relative to a magnetic resonance signal from venous blood providing a contrast between a coronary venous structure and surrounding myocardium in the magnetic resonance image; and
acquiring magnetic resonance imaging data from the coronary venous region to produce an image of the coronary venous structure.

2. The method of claim 1, wherein the coronary venous structure comprises at least one of a coronary sinus, a lateral vein and a posterior vein.

3. The method of claim 1, wherein the MT pulses are offset from the resonant frequency of water by 500 Hz or less.

4. The method of claim 1, wherein the MT pulses are offset from the resonant frequency of water by between 300 and 500 Hz.

5. The method of claim 1, wherein the train of MT pulses comprises 8 to 10 pulses.

6. The method of claim 1, wherein each pulse in the train has a pulse duration between 10 and 20 milliseconds.

7. The method of claim 1, wherein each pulse in the train has a flip angle between 800 degrees and 1000 degrees.

8. The method of claim 1, wherein all pulses in the train have a same shape and frequency response.

9. The method of claim 1, wherein the MT pulses vary in at least one of their shape and their frequency response across the train of pulses.

10. The method of claim 1, wherein the MT pulses include a shape that comprises one or more of Gaussian, Fermi, Sinc, and Gaussian-weighted Sinc.

11. The method of claim 10, wherein the pulse shape is Gaussian-weighted Sinc.

12. The method of claim 1, wherein the MT pulses are coordinated to a cardiac cycle of the subject.

13. The method of claim 12, wherein the MT pulses are initiated in response to a trigger signal from an electrocardiogram.

14. The method of claim 1, wherein during an imaging sequence including application of the MT pulses, a specific absorption rate of the subject is less than 1 watt per kilogram.

15. The method of claim 1, wherein the specific absorption rate is less than 0.8 watts per kilogram.

16. The method of claim 1, wherein the magnetic resonance imaging data is acquired with a gradient-echo acquisition sequence.

17. The method of claim 1, wherein the magnetic resonance imaging data is acquired with a steady-state free precession acquisition sequence.

18. The method of claim 1, further comprising performing a respiratory navigation between the application of the MT pulses and the acquisition of the magnetic resonance imaging data.

19. The method of claim 1, further comprising performing a breath-hold operation between the application of the MT pulses and the acquisition of the magnetic resonance imaging data.

20. The method of claim 1, further comprising applying a radiofrequency pulse to promote fat saturation in the coronary venous region between the application of the MT pulses and the acquisition of the magnetic resonance imaging data.

21. The method of claim 1, wherein the image of a coronary venous structure is acquired in connection with an interventional cardiovascular procedure.

22. The method of claim 21, wherein the procedure comprises a cardiac resynchronization therapy, 23. The method of claim 1, further including acquiring magnetic resonance imaging data using a thin slab placed on a lateral and posterior wall of the left ventricle.

24. The method of claim 1, further including acquiring magnetic resonance imaging data using whole heart imaging.

25. A magnetic resonance imaging system, comprising:
a system controller configured to define a train of magnetization transfer (MT) pulses, the MT pulses having a frequency that is offset from resonant frequency of water within a magnetic field, the MT pulses applied to suppress a magnetic resonance signal from myocardial tissue relative to a magnetic resonance signal from venous blood providing a contrast between a coronary venous structure and surrounding myocardium in the magnetic resonance image;
a radiofrequency coil that is controlled by the system controller to produce radiofrequency pulses that are transmitted to a coronary venous region of a subject located in the magnetic field, the system controller controlling the radiofrequency coil to produce the train of MT pulses followed by one or more imaging pulses; and
a receiver that acquires magnetic resonance imaging data in response to the imaging pulses to produce an image of the coronary venous structure.

26. The system of claim 25, wherein the train of MT pulses comprises 8 to 10 pulses.

27. The system of claim 25, wherein each pulse in the train has a pulse duration between 10 and 20 milliseconds.

28. The system of claim 25, wherein each pulse in the train has a flip angle between 800 degrees and 1000 degrees.

29. The system of claim 25, wherein all pulses in the train have a same shape and frequency response.

30. The system of claim 25, wherein the MT pulses vary in at least one of their shape and their frequency response across the train of pulses.

31. The system of claim 25, wherein shapes of the MT pulses comprises one or more of Gaussian, Fermi, Sinc, and Gaussian-weighted Sinc.

32. The system of claim 25, wherein the MT pulses are offset from the resonant frequency of water by between 300 and 500 Hz.

33. A non-transitory computer readable medium having a computer executable program for performing a magnetic resonance imaging (MRI) sequence, comprising:
applying a train of radiofrequency magnetization transfer (MT) pulses having a frequency that is offset from resonant frequency of water within a magnetic field to a coronary venous region of a subject located in a magnetic field subject, the MT pulses applied to suppress a magnetic resonance signal from myocardial tissue relative to a magnetic resonance signal from venous blood providing a contrast between a coronary venous structure and surrounding myocardium in the magnetic resonance image; and acquiring magnetic resonance imaging data to produce an image of the coronary venous structure.

* * * * *

UNITED STATES PATENT AND TRADEMARK OFFICE
CERTIFICATE OF CORRECTION

PATENT NO. : 8,457,711 B2
APPLICATION NO. : 12/011992
DATED : June 4, 2013
INVENTOR(S) : Reza Nezafat and Warren Manning Page 1 of 1

It is certified that error appears in the above-identified patent and that said Letters Patent is hereby corrected as shown below:

In the Claims:

In Column 12, line 17, Claim 22, delete "," and insert -- . --

In Column 12, line 54, Claim 31, delete "Sine" and insert -- Sinc --

In Column 12, line 55, Claim 31, delete "Sine" and insert -- Sinc --

Signed and Sealed this
Twentieth Day of August, 2013

Teresa Stanek Rea
*Acting Director of the United States Patent and Trademark Office*